US00PP11698P

United States Patent [19]

Beatson et al.

[11] Patent Number: Plant 11,698

[45] Date of Patent: Dec. 19, 2000

[54] APRICOT TREE NAMED 'GABRIEL'

[75] Inventors: Ron Beatson, Nelson; Dominique Noiton, Wellington, both of New Zealand

[73] Assignee: The Horticulture and Food Research Institute of New Zealand Limited, Palmerston North, New Zealand

[21] Appl. No.: 08/892,799

[22] Filed: Jul. 15, 1997

[51] Int. Cl.[7] ..... A01H 5/00

[52] U.S. Cl. ..... Plt./186

[58] Field of Search ..... Plt./39, 186

[56] References Cited

U.S. PATENT DOCUMENTS

P.P. 10,232 2/1998 Fear et al. ..... Plt./39

P.P. 10,233 2/1998 Fear et al. ..... Plt./39

OTHER PUBLICATIONS

GTITM UPOVROM Citation for 'Gabriel' as per NZ PBR SFM069, Oct. 14,1996.

*Primary Examiner*—Bruce R. Campell
*Assistant Examiner*—Kent L. Bell
*Attorney, Agent, or Firm*—Christie, Parker & Hale, LLP

[57] ABSTRACT

The present invention relates to a new and improved variety of apricot tree. The fruit of the new variety is characterized by an attractive deep orange color with a red blush, very large size, and firm flesh with sweet flavor. The tree is characterized by moderately vigorous healthy growth and spreading tree habit. The new variety has been named 'Gabriel'.

1 Drawing Sheet

ORIGIN OF THE VARIETY

The new and distinct variety of apricot tree (*Prunus armeniaca*) was selected from a population of approximately 2000 seedlings originated by Dr. Ron Beatson in 1986. The seedlings were grown on a site near Clyde, Central Otago, New Zealand's major apricot growing area. The seedlings began to fruit in 1990, and were evaluated for tree health and fruit flavor, and to a lessor extent skin finish, size and color. In 1993, 49 elite seedlings were selected by Dr. Dominique Noiton from this population and grafted onto rootstocks for further evaluation. One of the seedlings, an open-pollinated seedling of CluthaGold (a New Zealand variety that has been granted Plant Variety Rights in New Zealand on Jun. 16, 1988 under Grant No. 411, and in France on Jan. 2, 1997 under Grant No. 09961) showed desirable commercial characteristics after initial evaluation and was propagated for further trials. Furthermore the new and distinct variety has been named 'Gabrial'. Seedling rootstocks are routinely used in New Zealand for ease of propagation. 'Golden Queen' is a peach (*Prunus persica*) variety that is commonly used because it is readily available and easily propagated from stones. It is a relatively vigorous stock that imparts vigor to the scion variety similar to that of trees on their own roots. It also imparts some tolerance to bacterial diseases such as *Psuedomonas syringae*.

The present new apricot tree was first asexually propagated at Clyde, Central Otago, by budding onto Golden Queen peach rootstocks, the standard apricot rootstock in New Zealand. The resulting trees have propagated true-to-type showing that the distinctive characteristics are established and transmitted successfully through succeeding generations.

DESCRIPTION OF THE VARIETY

The new and distinct variety of apricot tree is of large size, moderately vigorous spreading growth habit, and is a regular and productive bearer of very large, firm, juicy fruit with very good sweet flavor and excellent eating quality. The fruit is further characterised by early-season ripening. 'Gabriel' is similar in appearance to the apricot 'Goldrich' (an unpatented American variety), however 'Gabriel' has bigger fruit size, and has smoother skin with a cleaner appearance.

BRIEF DESCRIPTION OF THE ILLUSTRATION

The accompanying photograph shows typical specimens of fruit and foliage of the new variety shortly after picking at commercial harvest maturity. The fruit is shown with the suture facing up (top right), view of the apex end (bottom right), side view (top left), view of the stern end (bottom left), a view of the fruit split along the suture line (top middle), and the stone (bottom middle).

DETAILED DESCRIPTION

The following is a detailed description of the new and distinct variety of apricot tree based on observation of the specimens grown near Clyde, Central Otago, New Zealand. Color code terminology (except those in common terms) is in accordance with The Royal Horticultural Society Colour Chart.

Tree:

*Size.*—The mature tree, from the age of six years and older is typically about 4 meters high by about 6 meters wide, when grown as a multi-leader vase-shaped tree; typically the amount of growth during one growing season (one year) on any shoot is about 600 to about 1000 mm; stem and caliper are typical of the species.

*Form.*—Spreading growth habit.

*Productivity.*—Typical production from a mature tree of five years or older is about 50 kg/tree.

*Bearing.*—Regular.

*Health.*—Very healthy.

Trunk:

*Form.*—Stocky.

*Texture.*—Rough.

*Color.*—Dark brown (200B).

Branches:

*Size.*—Medium thickness, long.

*Surface.*—Rough.

*Lenticels.*—Numerous, prominent, aligned across the direction of the branch (165D).
*Color of mature wood.*—Dark brown (200B).
*Color of fresh growth.*—Dark red (184A).

Leaves:
*Size.*—Between 80–90 mm long and 70–80 mm wide for mature leaves.
*Shape.*—Cordate.
*Shape of tip.*—Cuspidated.
*Angle of tip.*—Obtuse.
*Shape of base.*—Truncate.
*Petiole.*—About 45 mm long, 3–5 mm wide. Red coloration (184A) Upper surface grooved.
*Glands.*—Ranging from 1–4 with an average of 2. Positioned on upper portion of petiole.
*Margin.*—Serrate.
*Color.*—Upper side, green (146A). Lower side, green (146B).

Flower buds:
*Size.*—Medium.
*Length.*—Medium.
*Shape.*—Round, plump.
*Form.*—Free.
*Surface.*—Not pubescent.

Flowers:
*Blooming period.*—Bloom commences approximately on 26th October.
*Size.*—Medium, about 25 mm in diameter.
*Color.*—Near 155D.

Fruit:
*Maturity when described.*—Eating ripe.
*Date of picking.*—1st week of January.
*Size.*—Very large. Average diameter axially, 70 mm. Average transversely in suture plane, 60 mm.
*Weight.*—130–150 gm.
*Form.*—Ovate, slightly compressed on one side.
*Suture.*—Shallow, extends from stem to apex.
*Fruit base.*—Rounded.
*Fruit flavor.*—Sweet, low acid, typcial apricot flavor.
*Juice.*—The fruit will express juice if squeezed.
*Sugar content.*—12–15% Brix.
*Cavity.*—Rounded.
*Apex.*—Rounded.

Skin:
*Thickness.*—Medium.
*Texture.*—Smooth.
*Tendency to crack.*—None.
*Down.*—Scant, very short.
*Color.*—Deep orange colour (25A) with a bright red overblush (46B) on up to 25% of the fruit.

Flesh:
*Ripens.*—Evenly.
*Texture.*—Firm.
*Fibres.*—Small, few, tender.
*Flavour.*—Excellent, sweet.
*Eating quality.*—Excellent.
*Color.*—Near the skin, orange (25B). Near the stone, orange (25D).

Stone:
*Type.*—Freestone, some flesh adherence along ventral edge.
*Size.*—Typical of the species.
*Form.*—Ovoid.
*Base.*—Straight.
*Apex.*—Nearly rounded.
*Surface.*—Regularly pitted.
*Ridges.*—Two distinct ridges towards the sharp end of the stone running on each side of the suture plane.
*Color.*—Dark brown 177A.
*Tendency to split.*—None.

Use: Dessert.
*Market.*—Local and export.
*Keeping quality.*—Good.
*Shipping quality.*—Good.

The tree, flowers, and fruit may vary in slight detail due to variations in soil types, cultural practices and climatic conditions; the present botanical description is that of the variety grown near Clyde, Central Otago, New Zealand.

We claim:

1. A new and distinct variety of apricot tree named 'Gabriel', substantially as illustrated and described.

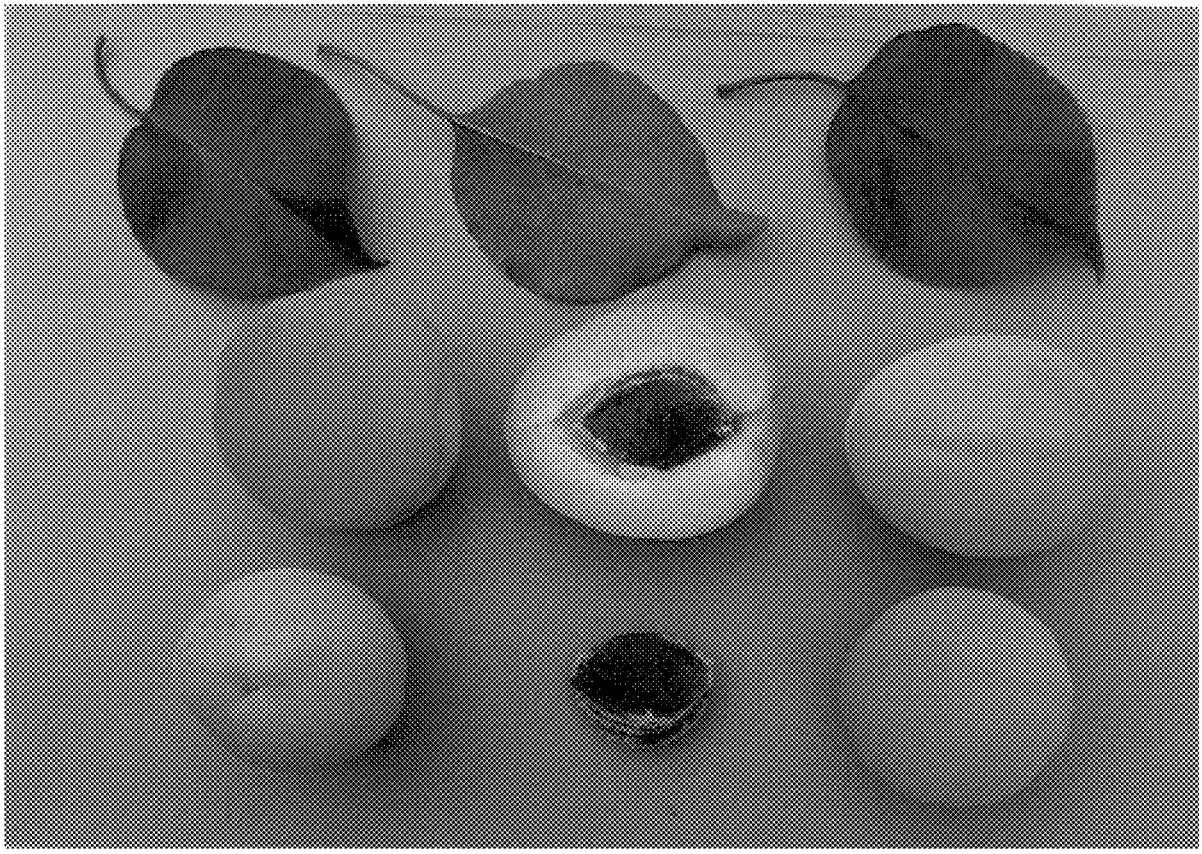

* * * * *